US008641758B1

(12) United States Patent
Anderson et al.

(10) Patent No.: US 8,641,758 B1
(45) Date of Patent: Feb. 4, 2014

(54) METHOD AND APPARATUS FOR INSERTING A FILLED PROSTHETIC BLADDER INTO A PATIENT

(76) Inventors: Robert G. Anderson, Fort Worth, TX (US); Bryan Hunt, Saratoga, TX (US)

(*) Notice: Subject to any disclaimer, the term of this patent is extended or adjusted under 35 U.S.C. 154(b) by 253 days.

(21) Appl. No.: 13/197,020

(22) Filed: Aug. 3, 2011

Related U.S. Application Data

(60) Provisional application No. 61/371,218, filed on Aug. 6, 2010.

(51) Int. Cl.
*A61F 2/12* (2006.01)
(52) U.S. Cl.
USPC ............. 623/8; 623/7; 623/23.64; 623/23.65; 623/23.7
(58) Field of Classification Search
USPC ............................ 623/7–8, 23.64–23.65, 23.7
See application file for complete search history.

(56) References Cited

U.S. PATENT DOCUMENTS

| | | | | |
|---|---|---|---|---|
| 3,216,420 A * | 11/1965 | Smith et al. | ..................... | 604/328 |
| 4,143,428 A * | 3/1979 | Cohen | ................................ | 623/8 |
| 4,641,648 A * | 2/1987 | Shapiro | ............................. | 606/1 |
| 4,955,906 A * | 9/1990 | Coggins et al. | ..................... | 623/8 |
| 5,041,102 A * | 8/1991 | Steer et al. | ..................... | 604/338 |
| 5,201,779 A * | 4/1993 | Shiao | ............................... | 606/91 |
| 5,549,672 A * | 8/1996 | Maddock et al. | .................. | 623/8 |
| 5,723,006 A * | 3/1998 | Ledergerber | ....................... | 623/8 |
| 6,726,660 B2 * | 4/2004 | Hessel et al. | .................... | 604/175 |
| 6,984,238 B2 * | 1/2006 | Gifford et al. | ................. | 606/155 |
| 7,056,326 B2 * | 6/2006 | Bolduc et al. | ................. | 606/153 |
| 7,413,569 B2 * | 8/2008 | Sogaard-Andersen | ....... | 606/151 |
| 7,566,337 B2 * | 7/2009 | Sogaard-Andersen et al. | ............................. | 606/151 |
| 7,691,151 B2 * | 4/2010 | Kutsko et al. | .............. | 623/23.65 |
| 7,731,651 B2 * | 6/2010 | Pearce et al. | ..................... | 600/37 |
| 7,935,089 B2 * | 5/2011 | Tsao | ............................. | 604/239 |
| 8,191,554 B2 * | 6/2012 | Kurz et al. | ..................... | 128/889 |
| 8,211,173 B2 * | 7/2012 | Keller et al. | ...................... | 623/7 |
| 8,409,279 B2 * | 4/2013 | Freund | .............................. | 623/8 |
| 2005/0049701 A1 * | 3/2005 | Brennan | .......................... | 623/8 |
| 2006/0074382 A1 * | 4/2006 | Gonzalez et al. | .......... | 604/93.01 |
| 2007/0038310 A1 * | 2/2007 | Guetty | ....................... | 623/23.72 |
| 2007/0093893 A1 * | 4/2007 | Studin | .............................. | 623/8 |
| 2009/0204107 A1 | 8/2009 | Keller et al. | | |
| 2009/0326676 A1 * | 12/2009 | Dupic et al. | ............... | 623/23.65 |
| 2010/0280610 A1 * | 11/2010 | Preissman | ........................ | 623/8 |
| 2011/0082546 A1 * | 4/2011 | Freund | .............................. | 623/8 |
| 2011/0264234 A1 * | 10/2011 | Baker et al. | ................ | 623/23.64 |

FOREIGN PATENT DOCUMENTS

WO    WO2008101048 A2 *   8/2008

OTHER PUBLICATIONS

Keller Funnel, Instructions for Use, Catalog # KS-005, Keller Medical, Inc., 2 pages.

\* cited by examiner

*Primary Examiner* — Thomas J Sweet
*Assistant Examiner* — Seema Mathew
(74) *Attorney, Agent, or Firm* — Geoffrey A. Mantooth

(57) ABSTRACT

The apparatus includes a funnel member, a coupling member and retractors. The funnel member is flexible and is frusto-conical in shape. The funnel member proximal end opening is larger than the distal end opening. The funnel member couples to a distal or coupling member that is located at the funnel member distal end portion. The distal or coupling member is rigid and has catches for removably coupling to the retractors. In use, the retractors anchor the apparatus to the patient while allowing the funnel member to be manipulated to force the prosthesis into a surgical cavity of a patient.

12 Claims, 5 Drawing Sheets

METHOD AND APPARATUS FOR INSERTING A FILLED PROSTHETIC BLADDER INTO A PATIENT

This application claims the benefit of provisional application, U.S. Ser. No. 61/371,218, filed Aug. 6, 2010.

FIELD OF THE INVENTION

The present invention relates to method and apparatuses for inserting prosthetic bladders, such as breast prostheses, into humans.

BACKGROUND OF THE INVENTION

Breast prostheses, or implants, are used in reconstructive and cosmetic surgery. A breast prosthesis is bladder-like, having an outer casing or membrane and an inner fluid substance. The inner fluid is either saline or silicone. The implants are inserted into cavities or pockets in the patient.

A saline implant can be inserted into a cavity in an empty configuration; once in place in the cavity, the implant is then filled with saline solution.

Preferably, the incision in the patient is small. Small incisions heal faster and are less unsightly. A saline prosthesis is relatively easy to implant through a small incision, as the bladder is unfilled and therefore small in size as it passes through the incision.

On the other hand, silicone implants are prefilled. Consequently, silicone implants are more difficult to pass through a small incision.

Keller, U.S. Publication No. 2009/0204107 discloses a device and method used to insert a silicone implant. While the device is useful, it suffers from some drawbacks. The device is used in a wet condition in order to ease the insertion of the implant. The wet condition reduces friction of the implant sliding through the device. Consequently, the device becomes slippery and is difficult to maintain in the incision. The device has no means of fixation to the patient or the incision, allowing it to slip out and contaminate the implant with skin bacteria. The Keller funnel also requires the surgeon to trim the funnel for each implant. Tape is used to form the funnel. The design relies on the tape maintaining the funnel's shape to break or "release" if the pressure on the implant becomes to great during the implant insertion process.

DESCRIPTION OF THE PREFERRED EMBODIMENT

Figure 1:
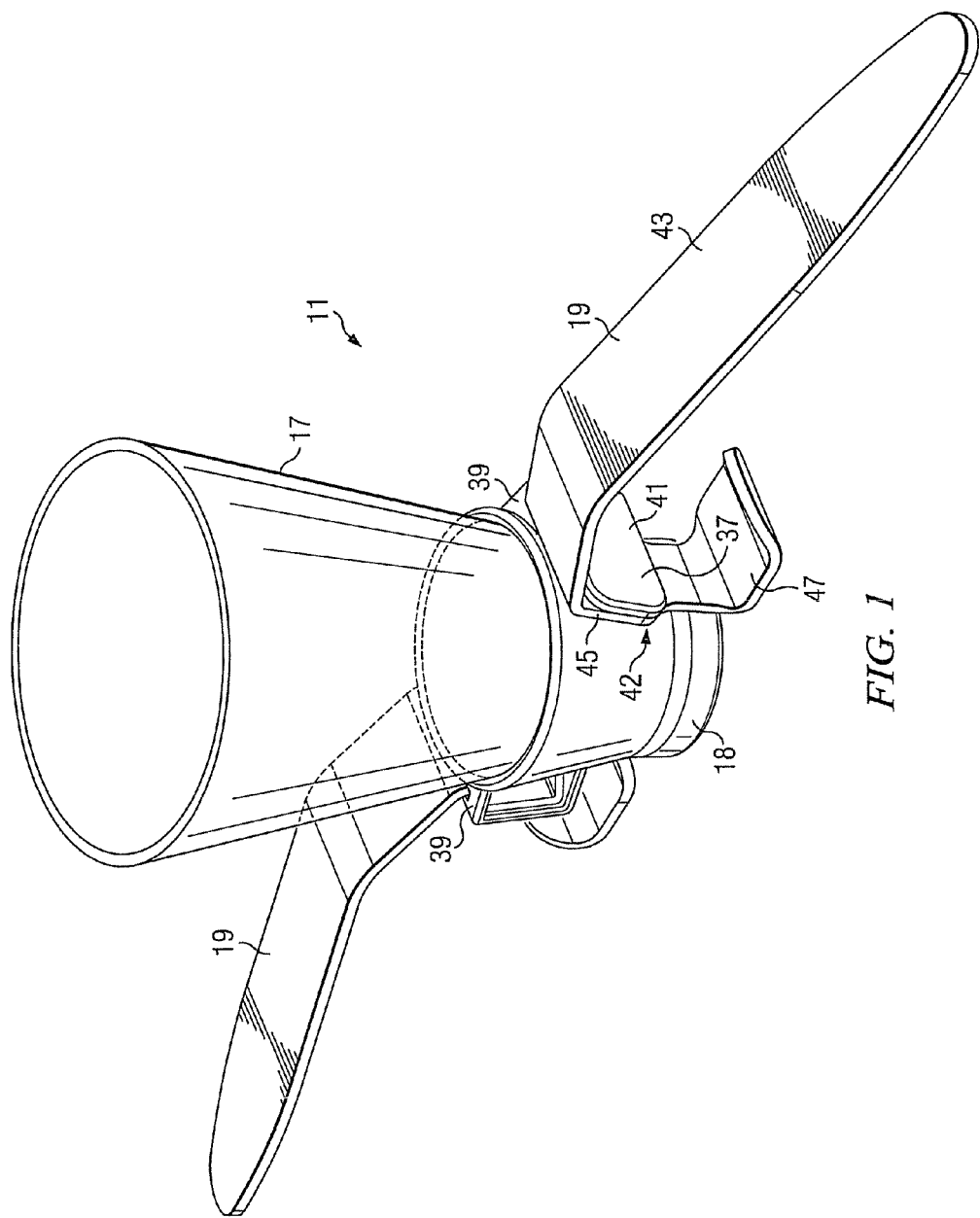
FIG. 1 illustrates the insertion apparatus.
Figure 2:
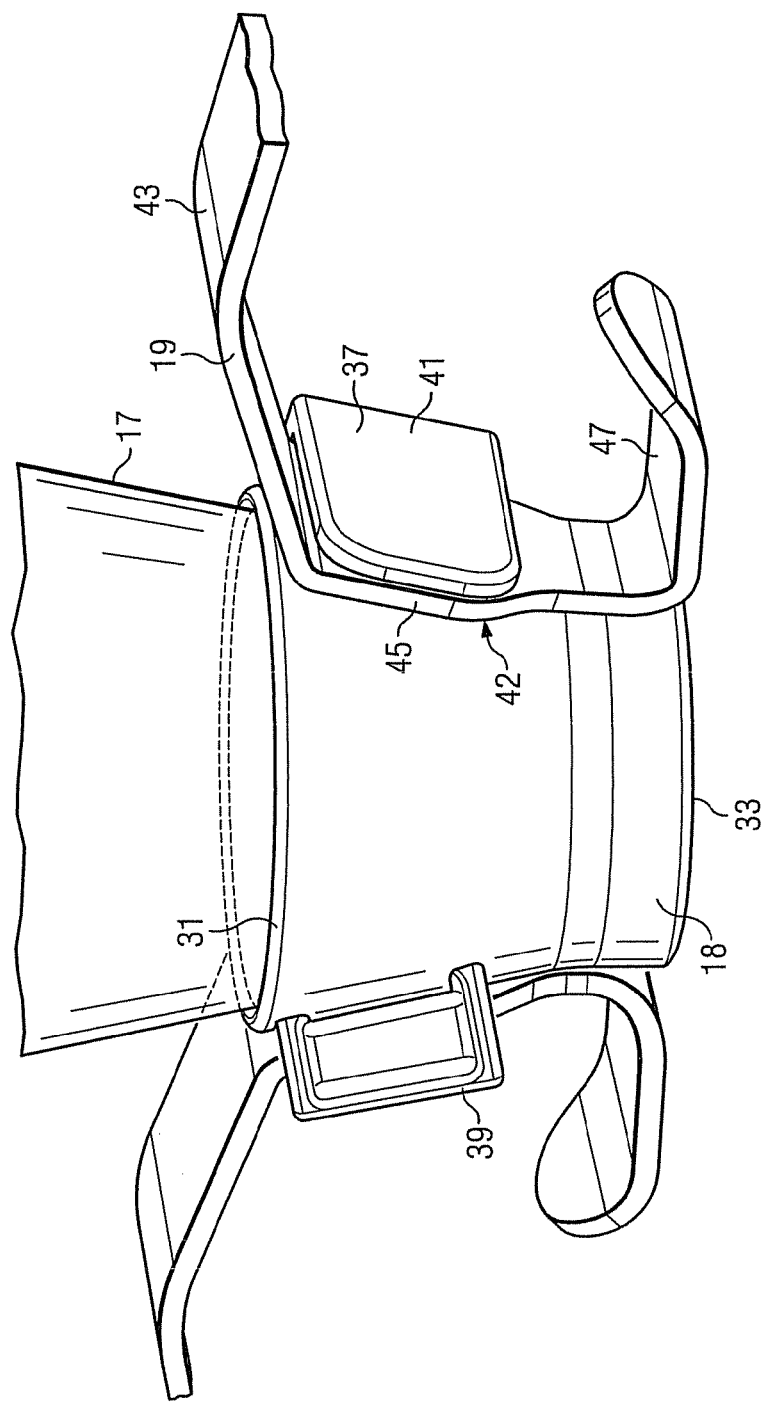
FIG. 2 is a close up view of the lower portion, or distal end, of the insertion apparatus.

Referring to the figures, the apparatus 11 is used to insert bladder-type prostheses 15 into a pocket or cavity 16 (see FIG. 4) of patients. The apparatus has a funnel member 17, a coupling member 18 and retractors 19.

The funnel member 17 is generally frusto-conical in shape, having proximal and distal ends 21, 23. The proximal and distal ends each have openings 25, 27, with the proximal opening 25 being larger in diameter than the distal opening 27.

The funnel member 17 is made of a sheet material such as plastic. For example, nylon can be used. The plastic may be strengthened or reinforced with fibers. The funnel member 17 is flexible. For example, the funnel member can be bent over onto itself and when it contains a prosthesis, can be squeezed about the prosthesis. The funnel member can also be twisted. Both squeezing and twisting are used to force the prosthesis into the body cavity.

The inner surface 29 of the funnel member 17 is preferably slick so as to allow the unhindered passage of the prosthesis. For example, a coating of surgical lubricant can be used on the inner surface. As an alternative, the funnel member can be provided with a coating that becomes slick when wet. In still another alternative, the prosthesis can be provided with a slick surface, such as a surgical lubricant.

Figure 4:
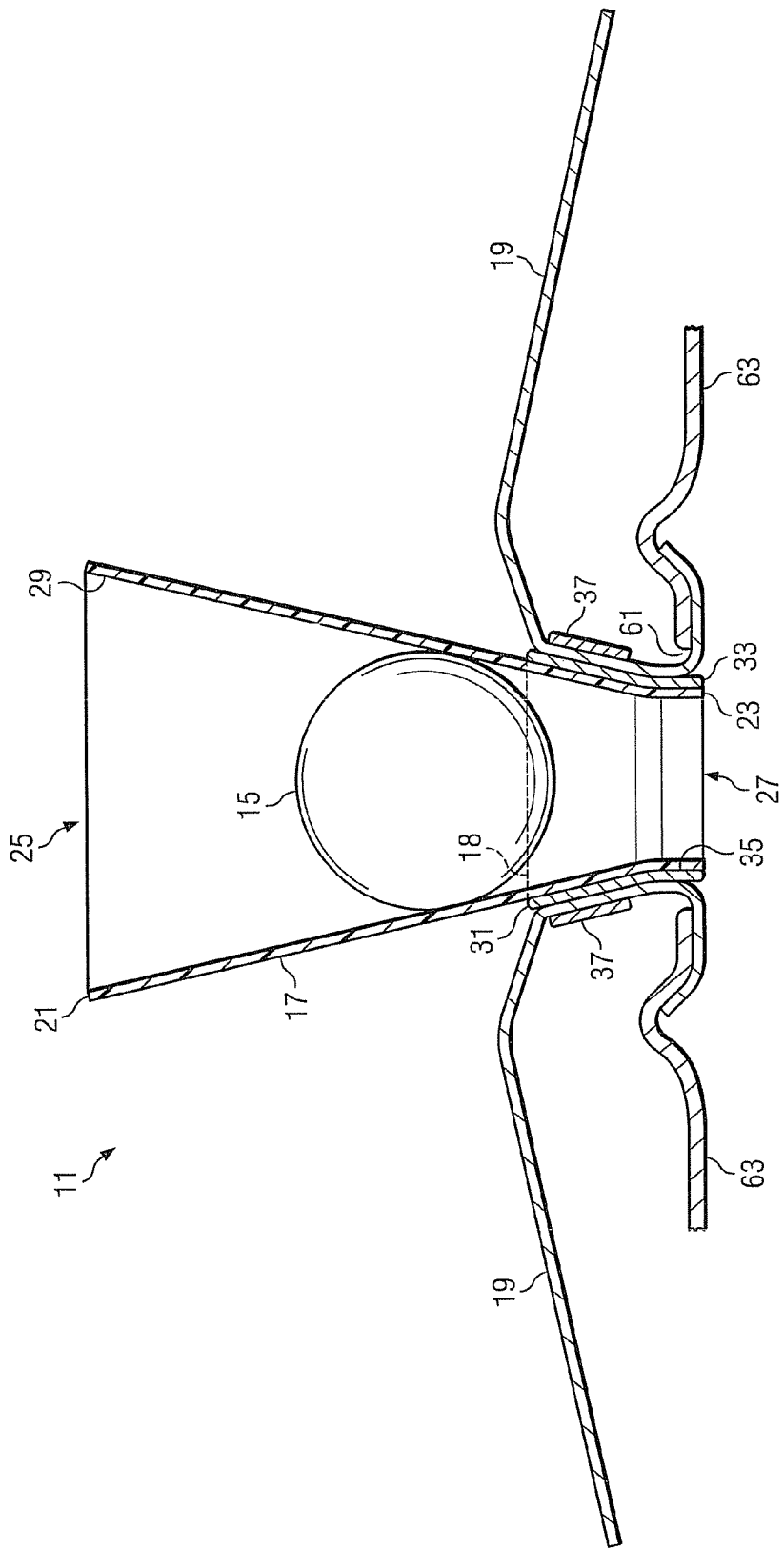
FIG. 4 is a cross-sectional view of the apparatus illustrating its use to insert a prosthesis into a body cavity.

The coupling member 18 is generally frusto-conical in shape and has an upper end 31 and a lower end 33 (referring to the orientation shown in the Figs.). The upper and lower ends 31, 33 have respective openings, with the upper end opening being larger in diameter than the lower end opening. The lower end portion of the coupling member can have a short section 35 extending from the lower end toward the upper end, which section has a constant inside diameter as shown in FIG. 4. Alternatively, the interior of the coupling member can have a sloped configuration all the way to the lower end.

The outside of the coupling member has "L" shaped catches 37. Each catch 37 has a short segment 39 that extends out from the coupling member and a longer segment 41 that extends parallel to a tangent of the exterior of the coupling member. An opening 42 is formed between the free end of the longer segment 41 and the body of the coupling member.

The coupling member is made of a rigid material such as metal (for example, stainless steel) or plastic.

The retractors 19 removably couple to the coupling member 18 at the catches 37. In the preferred embodiment, the apparatus uses two retractors 19, although additional retractors could be used if needed. Alternatively, a single retractor could be used. Each retractor 19 has a handle 43, an intermediate portion 45 and a distal end 47. The retractors can have various shapes and sizes to match the particular application.

The handle 43 of each retractor is bent or angled relative to the intermediate portion 45. This is so that when the retractor is coupled to the coupling member, the handle extends laterally from the funnel member 17, as shown in FIG. 4, so as not to interfere with the surgeon manipulating the funnel member proximal end 21. The handle is used for the insertion of the retractor into the patient and in coupling the retractor to the coupling member 18. The distal end 47 in the retractor has a flange that is angled relative to the intermediate portion. The distal end is structured and arranged to be inserted into a cavity of a patient. The distal end has a lip 49 that is bent toward the handle and that helps maintain the distal end of the retainer beneath skin tissue of a patient. The intermediate portions 45 of the retractors form an interference fit with the catches 37. Each intermediate portion ingresses and egresses the respective catch through the opening 42. The retractors 19 are made of metal, such as stainless steel.

To assemble the apparatus, the funnel member 17 is inserted into the coupling member and secured thereto. Double sided surgical tape can be used to couple the distal end portion 23 of the funnel member 17 inside of the coupling member 18. Alternatively, the funnel member can be coupled to the coupling member by glue or adhesive, heat bonding or other coupling mechanism.

Figure 5:
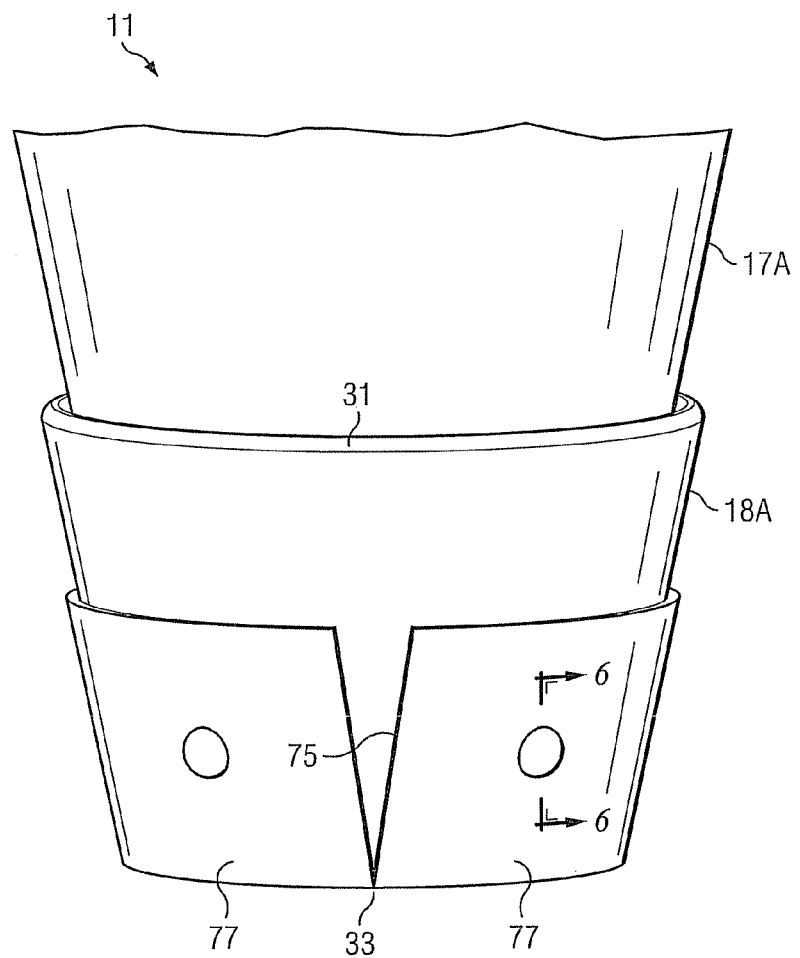
FIG. 5 is a close up view of the lower portion, or distal end, of the apparatus in accordance with another embodiment.
Figure 6:
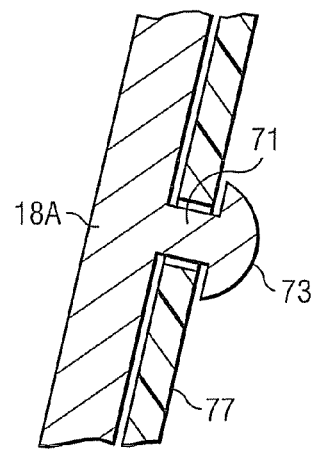
FIG. 6 is a cross-sectional view taken at lines VI-VI of FIG. 5.

FIGS. 5 and 6 show the apparatus in accordance with another embodiment that uses an alternative to couple the funnel, member to the coupling member. The coupling member 18A has catches near the proximal, or upper end, 31 (the catches are not shown in FIG. 5 or 6); the catches couple the retractors to the coupling member. The outside surface of the coupling member is provided with projections 71 that extend radially out and have an enlarged head 73. The distal end of the funnel member 17A is provided with longitudinally oriented slots 75 that extend from the distal end a short distance toward the proximal end of the funnel member. The slots 75 form flaps 77 in the distal end of the funnel member. Each flap has an opening that aligns with a respective projection 71 (see FIG. 6).

Figure 3:
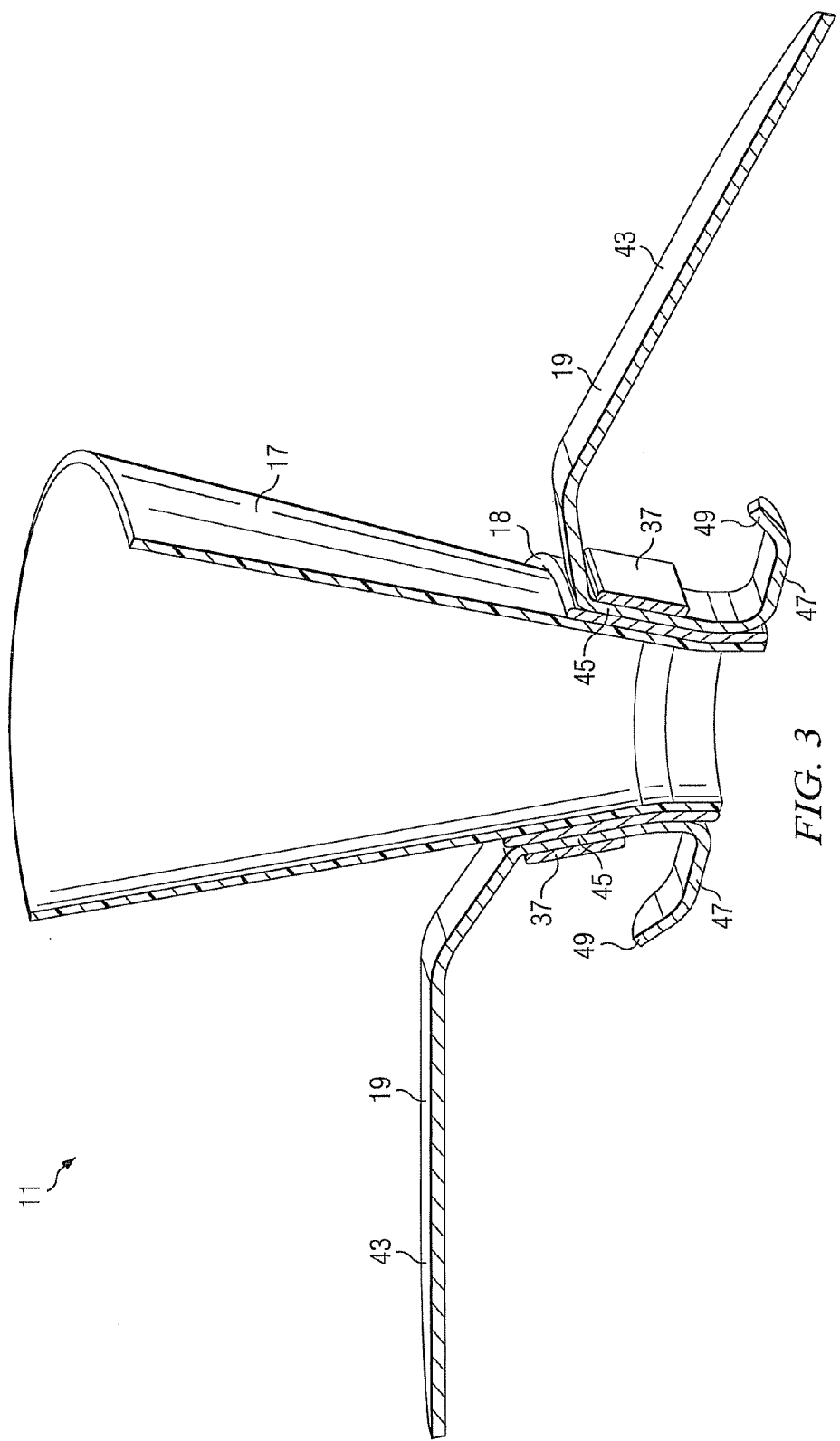
FIG. 3 is a cross-sectional view of the insertion apparatus, taken along the funnel member and coupling member.

To couple the funnel member 17A to the coupling member 18A, the distal end of the funnel member is inserted all the way through the coupling member so that the flaps 77 project from the coupling member distal end (the proximal end of the funnel member 17A extending away from the coupling member proximal end as in FIG. 3). The flaps 77 are folded back onto the coupling member, with the projections 71 being located in the openings. The enlarged heads 73 retain the flaps to the coupling member.

As an alternative to the projections 71, the funnel member flaps 77 can be secured to the outside of the coupling member with tape, snaps, glue or adhesive, heat bonding or other coupling mechanisms.

To use the apparatus 11, an incision 61 is made in the patient's skin 63. The incision is of an appropriate length so as to allow insertion of the retractors 19 and the distal end of the coupling member 18, 18A. The distal ends 47 of the retractors 19 are used to open the incision and allow the insertion of the coupling member distal, or lower, end 33 therein. The distal ends 47 of the retractors are inserted into the incision and located under the skin tissue 63 (see FIG. 4) and moved to open the incision. The coupling member distal end 33 is inserted into the now open incision. Once inserted, the coupling member 18 is rotated (clockwise from the surgeon's perspective) to locate the retractor intermediate portions 45 into the catches 37. Alternatively, the coupling member can be kept stationary while the retractors 19 are moved into the catches. Still another alternative is to fit a retractor to a coupling member and insert the coupling member and retractor into the incision. The other retractor, already in the incision, is then coupled to the coupling member.

The prosthesis 15 is located in the funnel member 17. A pocket or cavity 16 is located under the skin tissue, which cavity is to receive the prosthesis. The proximal end 21 and adjacent portions of the funnel member 17 are squeezed and/or twisted to force the prosthesis 15 toward the distal ends 23, 33, and into the cavity 16. The prosthesis deforms to fit through the distal end opening 27.

The apparatus 11 provides several advantages to the insertion procedure. One advantage is that the implant (prosthesis) can be inserted into a body cavity without the surgeon or assistant touching the implant. This technique provides a totally "no touch" technique for prosthesis insertion. Another advantage is that once the apparatus is located in the incision, it is anchored to the patient and will not pull out This gives the surgeon something to push against as the prosthesis is forced into the patient cavity. Consequently, it simplifies the insertion process. The funnel member is subjected to squeezing and/or twisting as the prosthesis is forced into the patient. Under such handling, the surgeon may unintentionally produce a pulling force on the funnel member. Without the retractors and coupling member, the funnel member would be pulled from the incision, (possibly contaminating the prosthesis) whereupon the distal end of the funnel member would have to be relocated into the incision.

Another advantage of the apparatus is that the coupling member 18 reinforces the funnel member 17 so that the funnel member will not tear. Without the coupling member, the force of the prosthesis passing through the funnel member distal end occasionally caused the distal end 23 to tear. The coupling member prevents this and maintains the funnel member intact.

Once the prosthesis is located inside the cavity, the retractors are uncoupled from the coupling member by relative rotation between the coupling member and the retainers. The coupling member is then removed from the incision, followed by the retractors. The incision can then be closed.

If the coupling member 18 and funnel member 17 are designed for single use, they are disposed of. If either the coupling member or funnel member are designed for reuse, they are subjected to sterilization procedures.

An advantage of the insertion apparatus and method is that the implant and insertion apparatus can be properly sized with respect to each other. A manufacturer of implants can provide the properly sized apparatus with the implant. The use of the coupling member 18 acts as a sizing cuff on the end of the funnel member. The size of the cuff is matched to the size of the implant. For example, some implants are physically large and require a cuff with a larger diameter distal opening, while other implants are physically smaller and can use a cuff with a smaller distal opening. By matching the insertion apparatus to the size of the implant, the chance that the implant will be damaged by excessive squeezing and stress is minimized. The implant is subject to damage if the implant is mishandled. Possible mishandling includes subjecting the implant to undue stresses or pressures, such as may be caused by attempting to squeeze the implant through an opening that is too small. A surgeon may make an incision in the patient that is too small for the implant and thus much force is required to squeeze the implant into the cavity. With the apparatus, the implant is protected from undue squeezing by the provision of the properly sized apparatus. A surgeon need not guess at what the proper size opening should be for the specific implant. The major complication with implants is capsular contracture thought to be due to sub-clinical infection. Subclinical infection is most likely caused by pushing the implant through the skin incision, dragging natural skin bacteria (still present after proper skin preparation) into the pocket surgically created for the implant. Use of this device prevents the implant from coming in contact with the skin during the insertion process.

Although the insertion member has been described in conjunction with retractors, it may be used without retractors. The insertion member comprises in this embodiment a funnel member and a rigid distal member. The distal member may be the same as the coupling member 18, except that the provisions for coupling to the retractors are not needed. The advantage to using this apparatus is that it minimizes the amount of pressure that can be applied to the prosthesis during insertion into a patient. The distal member is sized according to the specific prosthesis (for example, 440 cc). Thus during insertion, the prosthesis cannot be squeezed through an opening which is too small and is therefore not subjected to too much pressure or squeezing.

The foregoing disclosure and showings made in the drawings are merely illustrative of the principles of this invention and are not to be interpreted in a limiting sense.

The invention claimed is:

1. An apparatus for inserting a prosthesis through an opening into a surgical cavity, comprising:
   a) a funnel member having a proximal end and a distal end, the proximal end and the distal end each having openings, the proximal end opening being larger than the distal end opening, the funnel member being flexible and structured and arranged to receive a deformable prosthesis;
   b) a coupling member having a first end opening and a second end opening, the first end opening being larger than the second end opening, the distal end of the funnel member being located inside of the coupling member and adjacent to the coupling member second end opening, the funnel member fixedly coupled to the coupling member;
   c) retractors that removably couple to the coupling member, the retractors having distal ends that are adjacent to the funnel member distal end and are structured and arranged to engage edges of the surgical cavity opening, the distal ends being fixed relative to the coupling member once the retractors are coupled to the coupling member.

2. The apparatus of claim 1 wherein the coupling member is rigid.

3. The apparatus of claim 1 wherein the coupling member comprises catches for coupling to the retractors.

4. The apparatus of claim 3 wherein the retractors fit into the catches by way of an interference fit.

5. The apparatus of claim 1 wherein the retractors comprise handles that extend away from the funnel member, the handles being in addition to the retractors distal ends.

6. The apparatus of claim 1 wherein the funnel member couples to the coupling member by way of tape.

7. The apparatus of claim 1 wherein the funnel member couples to the coupling member by way of funnel member flaps and located about the coupling member distal end and secured to the coupling member.

8. The apparatus of claim 1, wherein:
   a) the coupling member is rigid;
   b) the coupling member comprises catches for coupling to the retractors;
   c) the retractors fit into the catches by way of an interference fit;
   d) the retractors comprise handles that extend away from the funnel member.

9. The apparatus of claim 7, wherein the funnel member flaps have openings that receive retainer pins on the coupling member.

10. The apparatus of claim 1, wherein the apparatus has a longitudinal axis between the funnel member proximal and distal ends, the retractors each having a coupling portion that couples to the coupling member, each of the coupling portions extending longitudinally, the distal end of each retractor extending radially, each retractor having a handle that extends away from the coupling member, the respective handle spaced apart from the respective retractor distal end by the respective coupling portion.

11. A surgical prosthesis insertion apparatus for use with a surgical cavity, the surgical cavity having an opening, comprising:
   a) a flexible prosthesis containment member having a proximal end portion and a distal end portion, the proximal end portion and the distal end portion each having openings, the distal end portion being a funnel that narrows to the distal end opening, the prosthesis containment member having an interior passage between the proximal end portion opening and the distal end portion opening;
   b) a deformable prosthesis located in the prosthesis containment member passage;
   c) a coupling collar fixedly coupled to the distal end portion of the prosthesis containment member, the prosthesis containment member distal end portion located between the passage and the coupling collar;
   d) retractors, each of the retractors comprising a handle and a distal end, each of the retractors being removably coupled to the coupling collar, wherein when the retractors are coupled to the coupling collar, the retractors are fixed relative to the coupling collar, the handles extend from the prosthesis containment member and the retractor distal ends extend radially out from the prosthesis containment member distal end portion so as to engage edges of the surgical cavity opening.

12. The apparatus of claim 11, wherein the prosthesis containment member has a longitudinal axis between the proximal and distal end portions, the retractors each removably coupling to the coupling collar by way of a coupling portion, each of the coupling portions extending longitudinally, the respective retractor handle spaced apart from the respective retractor distal end by the respective coupling portion.

* * * * *